United States Patent [19]

Wilting

[11] Patent Number: 5,757,877
[45] Date of Patent: May 26, 1998

[54] DETERMINING A DIMENSION FROM A DENSITY DISTRIBUTION

[75] Inventor: Jantje E. Wilting, Eindhoven, Netherlands

[73] Assignee: U.S. Philips Corporation, New York, N.Y.

[21] Appl. No.: 726,709

[22] Filed: Oct. 7, 1996

[30] Foreign Application Priority Data

Oct. 6, 1995 [EP] European Pat. Off. .............. 95202685

[51] Int. Cl.⁶ .................................................. A61B 6/03
[52] U.S. Cl. .............................. 378/8; 378/901; 382/131
[58] Field of Search ......................... 378/8, 901; 382/131

[56] References Cited

U.S. PATENT DOCUMENTS 5,528,644  6/1996  Ogawa et al. ............................. 378/8

FOREIGN PATENT DOCUMENTS

WO 87/00924   2/1987   WIPO .
WO8700924   12/1987   WIPO .

OTHER PUBLICATIONS

"Technical Optimization of Spiral CT for Depiction of Renal Artery Stenosis: In Vitro Analysis", by James A. Brink et al, Radiology 194 (1995) 157–163.

"Further Investigation and Initial Clinical Use of Advanced CT Display Capability", by William V. Glen et al, Investigative Radiology, vol. 10, Sep./Oct. 1975.

"Image Generation and Display Techniques for CT Scan Data", by William V. Glen et al, Investigative Radiology, vol. 10, Sep./Oct. 1975.

*Primary Examiner*—David P. Porta
*Assistant Examiner*—David Vernon Bruce
*Attorney, Agent, or Firm*—Jack D. Slobod

[57] ABSTRACT

A density distribution of an object to be examined is obtained, for example by X-ray computed tomography or magnetic resonance imaging, and an accurate dimension of a detail of the object is derived from density values of a corresponding relevant detail of the density distribution and density values outside the relevant detail. Preferably, a reduction of a maximum density value of the relevant detail is compensated on the basis of density values outside the relevant detail.

8 Claims, 2 Drawing Sheets

DETERMINING A DIMENSION FROM A DENSITY DISTRIBUTION

BACKGROUND OF THE INVENTION

1. Field of the Invention

The invention relates to a method of measuring a dimension of a detail of object from a density distribution of an object to be examined by deriving a dimension of the corresponding detail in the object from a detail of the density distribution. The invention also relates to methods for imaging, notably to a computed tomography method which includes irradiation of an object to be examined by means of X-rays from an X-ray source, detection of X-rays having traversed the object by means of a position-sensitive X-ray detector, the X-ray source and the X-ray detector being arranged together in a number of orientations relative to the object, reconstruction of a density distribution of the object to be examined on the basis of X-ray images detected in separate orientations, and deriving a dimension of the corresponding detail in the object to be examined from a detail of the density distribution. The invention also relates to an imaging system such as a computed tomography device which comprises an X-ray source for irradiating an object to be examined by means of X-rays, a position-sensitive X-ray detector for detecting X-rays having traversed the object to be examined, it being possible to arrange the X-ray source and the X-ray detector together in a number of orientations relative to the object, a reconstruction unit for reconstructing a density distribution of the object on the basis of X-ray images detected in individual orientations, and an arithmetic unit for deriving a dimension of the corresponding detail in the object from a detail of the density distribution.

2. Description of the Related Art

Such a method for deriving a dimension of a detail in the object from a density distribution of an object to be examined is known from the article "Technical optimization of spiral CT for depiction of renal artery stenosis: in vitro analysis" by James A. Brink et al., published in Radiology 194 (1995) 157–163.

The known method is intended to be carried out on a density distribution obtained by computed tomography performed on a patient to be examined. Said article by Brink et al. discloses an in vitro examination where computed tomography images are made of polyester tubes (pipettes) provided with constrictions of different dimensions and filled with an X-ray attenuating liquid. The authors utilize said pipettes to simulate vascular constrictions in a patient to be examined.

The known method aims to measure the degree of constriction of a blood vessel (in fact a polyester pipette). It is the object of the measurement to determine whether it is necessary and justified to treat a stenosis (constriction) of a blood vessel surgically or by interventions like so called Dotter-techniques. According to the known method the width of a detail of the density distribution, notably a profile, is measured as the width of the profile at $1/10$ of the maximum density value of the relevant detail (FWTM measurement) or as the width of the profile at a density value which excludes $1/10$ of the surface area of the profile (FWTA measurement). Said publication states that the width of a blood vessel (or polyester pipette) is often overestimated. Even though according to the known method the density distributions are averaged so as to counteract disturbances due to noise, it has been found that such a correction hardly mitigates inaccuracies in the measurement of dimensions of a blood vessel. It is a drawback of the known method that in critical cases a vascular constriction could be missed or unduly considered to be not serious.

It is an object of the invention to provide a method for deriving from a density distribution a value of a dimension of a detail of an object to be examined which is more accurate in comparison with that derived by means of the known method.

To achieve this, a method in accordance with the invention is characterized in that a value of the dimension of the corresponding detail of the object is derived from density values of a part of the density distribution outside said detail in the density distribution and from density values of said detail in the density distribution.

The density distribution of the object, for example a patient to be examined, can be recorded, for example by computed tomography utilizing X-rays, by forming a shadow image by irradiation by means of an X-ray beam, or by means of magnetic resonance imaging (MRI).

It has been found that inaccuracy, notably overestimation, of the dimension of a detail of the object to be examined, such as a blood vessel of a patient to be examined, is significant notably in the case of small dimensions of the detail. For a variety of reasons the boundaries of a detail of the density distribution are blurred. If no steps are taken, such blurring leads to inaccurate results in respect of the value of the dimension of the relevant detail. Blurring is to be understood to mean herein that a step-like density variation of the object appears as a more or less steep gradient in the recorded density distribution. For example, blurring occurs because of limited spatial resolution of an X-ray detector used for detecting X-rays having traversed the patient, because the X-ray beam does not emanate from exactly one point, or because of scattered X-rays. When a magnetic resonance method is used to record the density distribution, widening and/or blurring occurs due to the limited sensitivity of the receiving systems used to detect the magnetic resonance signals. Blurring influences notably the width of small details in the density distribution, but has less effect on a part of the density distribution outside such small details. It has been found that the dimension of a somewhat larger detail accurately corresponds to the width of the corresponding detail of the density distribution. It is possible to obtain an accurate value of the dimension of the relevant detail of the object to be examined by taking into account not only the corresponding detail of the density distribution, but also a part of the density distribution outside the relevant detail. In order to derive the value of the dimension, density values of said detail and outside said detail are then preferably chosen in such a manner that predetermined relationship exists with the densities of the parts of the object to be examined which correspond to said respective density values; preferably, use is made of density values which already relate to parts of the object which have substantially the same composition. Preferably, the exact value of the dimension of the relevant detail is obtained by calculation from density values of the corresponding detail of the density distribution and density values outside the relevant detail.

Accurate results are obtained by means of the method of the invention notably when blurring occurs mainly for density variations in a given direction in the object to be examined, whereas density variations in directions transversely of said given direction are blurred far less. Such a situation occurs notably in a density distribution obtained by means of X-ray computed tomography with so-called multiplanar reconstruction (MPR) where the reconstruction plane extends mainly perpendicularly to the plane of maximum resolution. It has been found that the blurring relating to the slice-sensitivity profile is far stronger than the blurring in the axial direction. MPR per se is know from the articles "Further investigation and initial clinical use of advanced CT display capability" and "Image generation and display techniques for CT scan data" by William V. Glen et al., Investigative Radiology, vol. 10, September/October 1975.

A preferred version of the method in accordance with the invention is characterized in that a corrected maximum value is derived from a maximum density value of said detail in the density distribution and from density values outside said detail, and that the value of the dimension of the corresponding detail in the object is derived from the width of the detail of the density distribution, the density value amounting to a predetermined fraction of the corrected maximum value.

It has been found that the overestimation of the dimension of a small detail is caused notably by the fact that the maximum density value of the corresponding detail of the density distribution has been reduced. A corrected maximum density value is derived from said reduced maximum density value and from density values outside the relevant detail, so that said reduction is compensated. The width of the relevant detail, for example a profile, of the density distribution corresponds exactly to the dimension of the relevant detail of the object to be examined for a predetermined fraction of said corrected maximum density value. It appears that the overestimation of the dimension of the detail is substantially mitigated by compensation of the reduction of the maximum density value.

A further preferred version of the method in accordance with the invention is characterized in that the corrected maximum value is derived from a maximum value of a part of the density distribution which relates to a second detail in the object to be examined, which second detail has a dimension which is substantially larger than that of said detail in the object to be examined which corresponds to said detail of the density distribution.

The second detail has a comparatively large dimension and, consequently, the maximum density value in the density distribution relating to said second detail has hardly been reduced. It is possible to achieve accurate composition of the reduction of the maximum density value of the smaller detail by suitably choosing the second detail with respect to the smaller detail whose dimension is to be measured. The maximum density value relating to the second detail is then compared with density values of the first detail. Using said accurately corrected maximum density value of the smaller detail of the density distribution, an exact value of the dimension of the detail in the object to be examined is derived as described above.

Furthermore, the first and the second detail in the object to be examined are preferably chosen so as to have a comparable, preferably substantially the same density. When the first detail is a narrow blood vessel, it is particularly advantageous to choose a larger blood vessel in the vicinity of said narrow blood vessel as the second detail or a wider part of the same blood vessel as the second detail.

Accurate results regarding the value of the dimension of a detail of the object to be examined are achieved notably by deriving said dimension from the width of the corresponding detail of the density distribution at the fraction ½ of the corrected maximum density value.

Each of the above versions of the method in accordance with the invention is suitable for notably density distributions of a patient to be examined which have obtained by means of various imaging methods, for example, X-ray computed tomography (CT scan), irradiation by means of an X-ray beam, or by means of magnetic resonance imaging (MRI).

Imaging can be performed in various ways. For example, imaging can be performed by computed tomography in which an object to be examined is irradiated by means of X-rays from an X-ray source and X-rays having traversed the object are detected by means of a position-sensitive X-ray detector, the X-ray source and the X-ray detector being positionable together in a number of orientations relative to the object, a density distribution of the object to be examined being reconstructed on the basis of X-ray images detected in separate orientations and from a detail of the density distribution there being derived a dimension of the corresponding detail in the object to be examined. An image of a slice of the object to be examined can be derived from the density distribution obtained by so-called multiplanar reconstruction of the individual X-ray images. Imaging can also be performed by radiological examination of an object by irradiating the object by means of an X-ray beam from an X-ray source and by detecting radiation having traversed the object to be examined by means of an X-ray detector arranged opposite the X-ray source, a density distribution being derived as a shadow image from the X-rays detected. Furthermore, imaging can be performed by magnetic resonance imaging of an object to be examined by arranging said object in a static magnetic field, by generating an electromagnetic excitation signal, and by generating temporary magnetic gradient fields in order to generate location-dependent magnetic resonance signals so as to derive a density distribution of the object from the magnetic resonance signals.

It is a further object of the invention to provide a computed tomography (CT) device for deriving a value of a dimension of a detail of an object to be examined from a density distribution of the object to be examined, said value being more accurate than that measured by means of a conventional CT device. To achieve this, a computed tomography device in accordance with the invention is characterized in that the arithmetic unit is arranged to derive a value of the dimension of the corresponding detail of the object from density values of a part of the density distribution outside said detail in the density distribution and from density values of said detail in the density distribution. A computed tomography device in accordance with the invention is suitable for carrying out the aforementioned methods.

These and other aspects of the invention will be apparent from and elucidated with reference to the embodiments described hereinafter.

DESCRIPTION OF THE PREFERRED EMBODIMENTS

Figure 1:
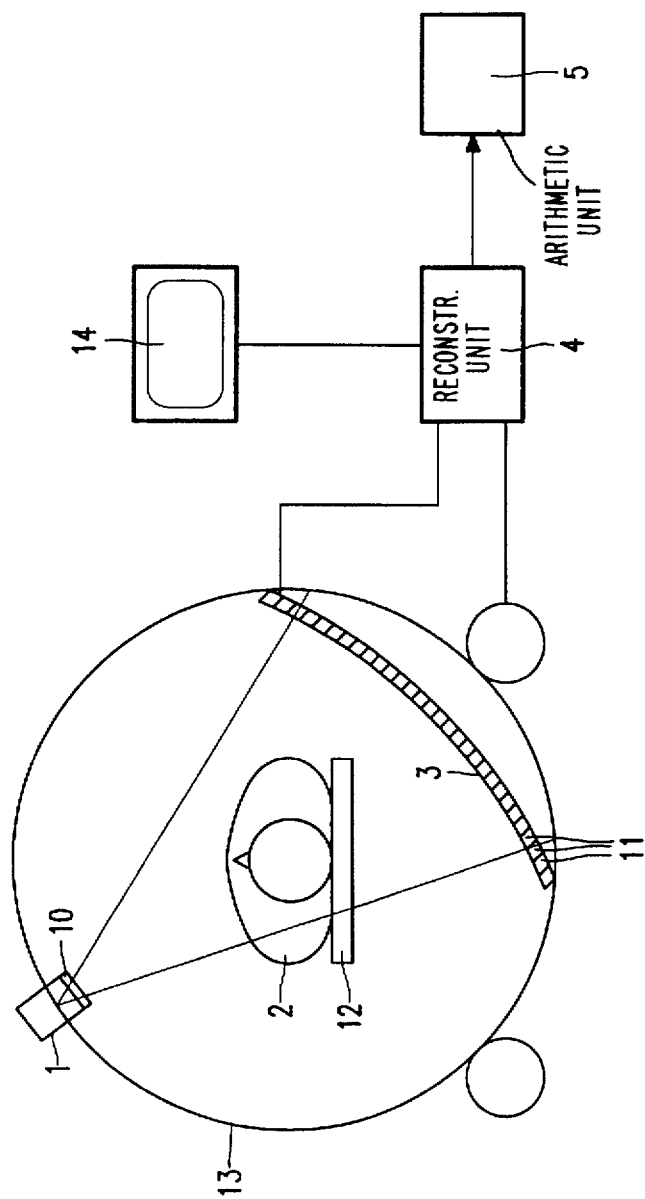
FIG. 1 is a diagrammatic representation of a computed tomography device in accordance with the invention.

FIG. 1 shows diagrammatically a computed tomography device in accordance with the invention. An X-ray source 1 cooperates with a slit-shaped diaphragm 10 so as to emit a diverging flat (fan-shaped) X-ray beam for irradiating the object 2, for example a patient 2 to be examined. The X-ray detector 3 is arranged opposite the X-ray source 1. The X-ray detector of the present embodiment is a position-sensitive X-ray detector comprising a row of separate detector cells 11. The detector cells 11 are, for example gas-filled (xenon) detectors or solid-state detectors. The thickness of the fan-shaped X-ray beam generally amounts to from 1 mm to 10 mm halfway between the X-ray source and the X-ray detector. The intensity of the radiation having traversed the patient and incident on the X-ray detector is determined mainly by the absorption within the patient 2 arranged on a table 12 between the X-ray source and the X-ray detector. The absorption is measured along a large number of lines from a large number of directions by rotating the X-ray source 1 and the X-ray detector 3 together around the patient by means of a support 13. The combined rotation of the X-ray source and the X-ray detector may be continuous but also intermittent. Furthermore, the patient can be displaced along the axis of rotation during irradiation and rotation, so that the X-ray detector acquires data from a significant three-dimensional volume of the patient. In addition to a rotatable assembly with an X-ray source and an X-ray detector, the computed tomography device may also comprise a detection system which is not rotatable but extends along (substantially) the entire circumference of the patient. Generally speaking, the X-ray source and the X-ray detector assembly are rotated completely, i.e. 360°, around the patient. Alternatively, use can be made of a detection system extending along the entire circumference of the patient, in which case the X-ray source is rotated completely around the patient. Furthermore, for the X-ray source use can also be made of an annular anode arranged around the patient, the point of incidence of an electron beam generating X-rays from the anode material then being displaced along the annular anode around the patient. It suffices in principle, however, to use a fan-shaped beam which also rotates around the patient through an angle which amounts to the sum of 180° and the angle of aperture of the fan-shaped beam.

In any position or orientation of the X-ray source and the X-ray detector the intensity of the X-rays received by the individual detector cells is digitized and applied to a reconstruction unit 4. In the reconstruction unit 4 this measured data is converted, after correction for known error sources and disturbances, into a density distribution of the patient to be examined. For example, high and low density values which correspond to parts of the patient in which the X-ray absorption is high and low, respectively, occur in the density distribution. Furthermore, an image of a slice along a plane through the patient can be derived from the density distribution by means of the reconstruction unit. An image of this kind may represent, for example a cross-section of the patient to be examined. Such an image can be displayed on a monitor 14 coupled to the reconstruction unit. The image may also be stored as a digital image matrix or be applied to an image processing unit for further processing. The computed tomography device also comprises an arithmetic unit 5 which is coupled to the reconstruction unit 4. The reconstruction unit 4 supplies the density distribution to the arithmetic unit. The arithmetic unit derives accurate values of dimensions of details of the patient, such as the diameter of blood vessels, from the density distribution.

In a contemporary X-ray examination apparatus, such as a computed tomography device, and in a contemporary device for forming an image by means of magnetic resonance, the dimension of the relevant detail can be derived by means of a suitably programmed computer or a special-purpose electronic processor.

Figure 2:
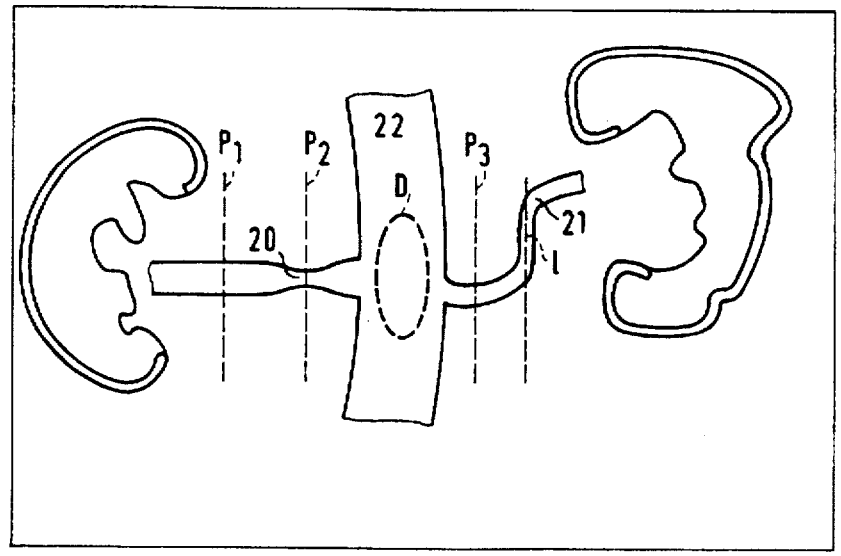
FIG. 2 shows schematically a density distribution obtained by means of a computed tomography device.

FIG. 2 schematically shows a density distribution in the form of an image of a cross-section of a patient to be examined as obtained by means of a computed tomography device with multiplanar reconstruction.

Grey values in the density distribution represent density values. For example, parts having high density values may be shown in white and parts having a low density value in black. The density distribution comprises a few details 20, 21 which correspond to blood vessels whose diameter is to be derived in several locations. The density distribution also comprises a larger detail 22. For anatomical information it may be derived that the density of the larger detail 22 is substantially the same as that of the details 20, 21. In the example shown the small detail 20 relates, for example to a vascular constriction. In order to make a suitable diagnosis, it is important that the diameter of the constricted vessel is accurately measured. Depending on the diameter of the constricted vessel, the physician may decide for surgery or treatment by medication.

Figure 3:
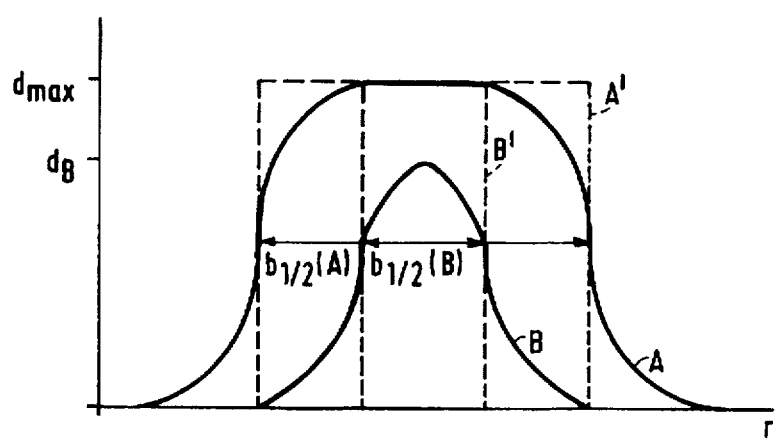
FIG. 3 shows profiles with different dimensions of density values of separate details of the density distribution of FIG. 2.

FIG. 3 shows profiles of density values of separate details of various dimensions of the density distribution of FIG. 2. In the ideal case such a profile would be substantially block-shaped, but in practice the edges are blurred and the profiles are slightly smeared. Blurring is due notably to the finite resolution of the system. In the case of computed tomography, the blurring in the axial direction, i.e. the direction transversely of the longitudinal direction of the patient to be examined so approximately in the plane of the fan-shaped beam, is due to, for example the finite width of the sensitive surface of the individual detector cells and also due to the fact that the fan-shaped beam does not emanate from an exactly point-shaped focus. In the longitudinal direction blurring is related to the so-called slice sensitivity profile. This means that in the longitudinal direction, i.e. the direction transversely of the plane of the fan-shaped X-ray beam, blurring occurs notably because the X-ray beam has a finite thickness and also because of the step magnitude of the displacement or the speed of displacement of the patient along the axis of rotation. Scattering of X-rays within the patient also contributes to blurring. It has been found that the measured profiles, in which blurring occurs to a varying extent as shown in FIG. 2, are suitably approximated by the convolution of the ideal block-shaped profile with a bell-shaped profile, for example a Gaussian or Lorentz profile. In a profile relating to a comparatively large detail the blurring at the edges of the profile is comparatively insignificant relative to the dimensions of the profile. Mainly at low density values the profile is widened. Therefore, an FWTM measurement of the width of the profile yields an overestimation of the dimension of the corresponding detail (width of the blood vessel) in the patient. The width ($b_{1/2}$) of the profile approximately halfway the maximum density value (FWHM) of the profile yields a more accurate value of the dimension of the detail. This is because blurring occurs notably at the edges of the relevant profile, so that blurring has a comparatively greater effect on the accuracy with which the dimension of a small detail can be determined. If blurring were not taken into account, the dimensions of details smaller than the width of the slice-sensitivity profile, for example 3 mm could not be determined accurately enough to make a diagnosis on the basis thereof. In the case of details of smaller dimensions not only blurring of the measured profile occurs, but the maximum density value of the profile is also found to be significantly reduced. If the width of said profile were measured at a fraction of said reduced maximum, the dimension of the relevant detail would be overestimated because the width of the profile would be then taken at the part with comparatively low density values which is substantially widened. The method in accordance with the invention corrects the maximum density value of the profile, so that the reduction of said maximum density value is compensated. Because the width of the profile is taken at a predetermined fraction (preferably half) of the corrected maximum density value, a substantial disturbance of the measurement of the dimension of the relevant detail by blurring, leading to widening particularly at low density values, is counteracted.

The extraction of the dimension of a detail from the width of the corresponding detail of the density distribution will be described in detail hereinafter with reference to some profiles as shown in FIG. 3. Profile A is associated with a comparatively large detail, such as a comparatively wide part (designated P1) of the blood vessel 20, of the density distribution. The ideal profile corresponding to the same detail in the patient to be examined, for example a blood vessel, is shown as a dashed block A'. For the profile A the width $b_{1/2}$ (A) of the profile at half the maximum density value $d_{max}$ corresponds exactly to the width of the ideal profile A', so that an accurate value of the dimension of the relevant blood vessel can be derived by means of the value of $b_{1/2}$ (A).

Profile B is associated with a smaller detail, for example a somewhat narrower part of the blood vessel 20 (designated P2). Because of the various causes of blurring, the profile has been widened with respect to the ideal profile B', but notably the maximum density value $d_B$ of the profile B has been reduced with respect to $d_{max}$. The maximum density value $d_{max}$ is derived from the profile A as the corrected maximum density value for the profile B. When the width of the profile B is taken at half the maximum density value $d_{max}$, it appears that the width $b_{1/2}$ (B) corresponds exactly to the width of the corresponding ideal block-shaped profile B'.

Evidently, it is alternatively possible to use density values of another detail expected to have substantially the same density. In the example $d_{max}$ can also be derived from the mean density value in a part D of the larger detail 22 which represents the aorta. It is furthermore possible to use a part of a detail which extends mainly in the direction of maximum blurring. For example, the maximum density value along the line 1 can be used to derive the diameter at the area of the position P3.

It has been found that the method in accordance with the invention produces accurate results for the dimensions of the relevant details in the patient, notably blood vessels, if said details have a dimension larger than the typical width say FWHM of the blurring profile, such as a Gaussian or Lorentz distribution whereby the blurring is represented. Even for details of a dimension only slightly smaller than the width of the blurring profile the method in accordance with the invention produces a value of the width of such a detail which deviates no more than 10% from the actual dimension of the detail. It has been found that the invention enables accurate determination of the diameter of blood vessels of a diameter of 3 mm, which are image with a slice thickness of 3 mm. This means that, for example, in rental artery of a diameter of 6 mm a stenosis of 50% can be accurately measured.

I claim:

1. A method of measuring a spatial dimension of a detail of an object from a reconstructed density distribution of the object, comprising deriving corresponding detail in the object to be examined from a detail of the density distribution, a value of the dimension of a corresponding detail of the object from density values of a part of the reconstructed density distribution outside said detail, and from density values of said detail in the reconstructed density distribution.

2. A method as claimed in claim 1, wherein a corrected maximum value is derived from a maximum density value of said detail in the reconstructed density distribution and from density values outside said detail, and the value of the dimension of the corresponding detail in the object is derived from the width of the detail of the reconstructed density distribution, the density value amounting to a predetermined fraction of the corrected maximum value.

3. A method as claimed in claim 2, wherein the predetermined fraction is ½.

4. A method as claimed in claim 2, wherein the corrected maximum value is derived from a maximum value of a part of the reconstructed density distribution which relates to a second detail in the object to be examined, which second detail has a dimension which is substantially larger than that of said detail in the object to be examined which corresponds to said detail of the reconstructed density distribution.

5. A method as claimed in claim 4, wherein the predetermined fraction is ½.

6. An imaging system comprising a device for reconstructing a density distribution of an object to be examined, and an arithmetic device which is arranged to derive a value of a spatial dimension of a corresponding detail of the object from density values of a part of the reconstructed density distribution outside said detail, and density values of said detail in the reconstructed density distribution.

7. A computed tomography device, comprising:

an X-ray source for irradiating an object to be examined with X-rays, an X-ray detector for detecting X-rays having traversed the object to be examined, the X-ray source and the X-ray detector being positionable together in a number of orientations relative to the object, a reconstruction unit for reconstructing a density distribution of the object to be examined on the basis of X-ray images detected in separate orientations, and an arithmetic unit for deriving a value of the dimension of a corresponding detail of the object from density values of a part of the reconstructed density distribution outside said detail, and density values of said detail in the reconstructed density distribution.

8. An imaging method comprising reconstructing a density distribution of an object, and deriving a value of a spatial dimension of a corresponding detail in the object from density values of part of the reconstructed density distribution outside and detail, and density values of said detail in reconstructed density distribution.

* * * * *